United States Patent
Muske et al.

(10) Patent No.: US 12,205,721 B1
(45) Date of Patent: Jan. 21, 2025

(54) SYSTEM AND METHOD FOR DIAGNOSING, DETERMINING TREATMENT, AND DETERMINING PROGNOSIS OF HEALTH, PERFORMANCE, FITNESS, TRAINING REGIMEN, AND BREEDING CONDITION OF AN ANIMAL SUBJECT USING EXPERT SYSTEMS, DATA INTEGRATION, IMAGING, AND 3D SCANNING TECHNOLOGY

(71) Applicants: Scott Phillip Muske, Encinitas, CA (US); Joy Sargis Muske, Encinitas, CA (US)

(72) Inventors: Scott Phillip Muske, Encinitas, CA (US); Joy Sargis Muske, Encinitas, CA (US)

( * ) Notice: Subject to any disclaimer, the term of this patent is extended or adjusted under 35 U.S.C. 154(b) by 1115 days.

(21) Appl. No.: 16/931,931

(22) Filed: Jul. 17, 2020

(51) Int. Cl.
| | | |
|---|---|---|
| *G16H 50/20* | (2018.01) | |
| *A61B 5/11* | (2006.01) | |
| *G06F 3/01* | (2006.01) | |
| *G16H 10/60* | (2018.01) | |
| *G16H 20/30* | (2018.01) | |
| *G16H 50/30* | (2018.01) | |

(52) U.S. Cl.
CPC ............. *G16H 50/20* (2018.01); *A61B 5/11* (2013.01); *G06F 3/011* (2013.01); *G16H 10/60* (2018.01); *G16H 20/30* (2018.01); *G16H 50/30* (2018.01); *A61B 2503/40* (2013.01)

(58) Field of Classification Search
USPC .......................................................... 703/11
See application file for complete search history.

(56) References Cited

U.S. PATENT DOCUMENTS

2021/0085240 A1* 3/2021 Pena ..................... A61B 5/1116

OTHER PUBLICATIONS

Photogrammetry. (Nov. 23, 2020). Wikipedia, the free encyclopedia. Retrieved May 25, 2023, from https://en.wikipedia.org/wiki/Photogrammetry (Year: 2020).*

Hohmann, Erik, Klaus Wörtler, and Andreas B. Imhoff. "MR imaging of the hip and knee before and after marathon running." The American journal of sports medicine 32.1 (2004): 55-59. (Year: 2004).*

Debarba, Henrique Galvan, et al. "Augmented reality visualization of joint movements for physical examination and rehabilitation." 2018 IEEE Conference on Virtual Reality and 3D User Interfaces (VR). IEEE, 2018. (Year: 2018).*

Soroko, Maria, and Kevin Howell. "Infrared thermography: Current applications in equine medicine." Journal of Equine Veterinary Science 60 (2018): 90-96. (Year: 2018).*

Alshafeey, Ghailan A., et al. "Augmented reality for the disabled: review articles." Journal of ICT in Education 6 (2019): 46-57. (Year: 2019).*

Drawings Pena, Armando. "Digital Platform to Identify Health Conditions and Therapeutic Interventions Using an Automatic and Distributed Artificial Intelligence System." Pub. No. US 2021/0085240 A1. Effective Filing Date: Dec. 20, 2018 (Year: 2018).*

* cited by examiner

*Primary Examiner* — G. Steven Vanni
*Assistant Examiner* — Dylan C Jones
(74) *Attorney, Agent, or Firm* — Plager Schack LLP; Mark H. Plager; Stephen Hallberg (57) ABSTRACT

A system and method for diagnosing, determining treatment, and determining prognosis of health, performance, fitness, training regimen, and breeding condition of an animal subject using expert systems, data integration, imaging and 3D scanning technology are disclosed. The system and method uses data integration, imaging and 3D scanning technology and other methods to collect data in a very precise and repeatable process. The system and method uses an AI expert system with deep learning analysis to analyze health history of an animal, performance of the animal, and breeding potential of the animal. This approach provides a highly accurate, repeatable and unbiased method to evaluate an animal and to recommend diagnosis and treatment.

12 Claims, 5 Drawing Sheets

SYSTEM AND METHOD FOR DIAGNOSING, DETERMINING TREATMENT, AND DETERMINING PROGNOSIS OF HEALTH, PERFORMANCE, FITNESS, TRAINING REGIMEN, AND BREEDING CONDITION OF AN ANIMAL SUBJECT USING EXPERT SYSTEMS, DATA INTEGRATION, IMAGING, AND 3D SCANNING TECHNOLOGY

BACKGROUND

Embodiments of the invention described in this specification relate generally to animal health and fitness evaluation, and more particularly, to an animal health, performance, fitness, training regimen, and breeding potential assessment system and a method for diagnosing, determining treatment, and determining prognosis of health, performance, fitness, training regimen, and breeding condition of an animal subject using expert systems, data integration, imaging and 3D scanning technology.

Animals, such as horses, are used for sport and are often bred and conditioned to race and perform in one or more sports. Currently, there is no existing method or process to consistently and independently evaluate and diagnose an animal's health, performance, and breeding potential. Conventionally, the present method for assessing a horse's health is by visual inspection from a trainer, an owner, a breeder, or a veterinarian. As such, determinations of fitness for breeding, state of conditioning, and whether to purchase animals, especially horses, are presently subjective and rely on the expertise and opinions of trainers, veterinarians, owners, or others. The assessments of different evaluators can therefore vary because the nature of the conventional method is highly subjective and can be easily influenced by competing business and personal objectives.

Therefore, what is needed is a way to accurately and objectively assess an animal's health, performance, and breeding potential in a repeatable, consistent, and unbiased manner, including application to a human subject (e.g., a professional athlete to track the effects of training and competition on the body).

BRIEF DESCRIPTION

A novel animal health, performance, fitness, training regimen, and breeding potential assessment system and method are disclosed for diagnosing, determining treatment, and determining prognosis of health, performance, fitness, training regimen, and breeding condition of an animal subject using expert systems, data integration, imaging and 3D scanning technology. In some embodiments, the animal subject is a horse. In some embodiments, the animal subject is a human. In some embodiments, the animal subject is a bovine animal (also referred to as "bovine" or "cow" in this disclosure). In some embodiments, the animal subject is an exotic animal. In some embodiments, the animal health, performance, fitness, training regimen, and breeding potential assessment system and the method for diagnosing, determining treatment, and determining prognosis of health, performance, fitness, training regimen, and breeding condition of an animal subject utilize expert systems, data integration, imaging and 3D scanning technology, and other methods, systems, and/or technology to collect data in a very precise and repeatable manner. In some embodiments, the animal health, performance, fitness, training regimen, and breeding potential assessment system is a scalable system that accommodates different sizes of different animal subjects.

In some embodiments, the animal health, performance, fitness, training regimen, and breeding potential assessment system includes (i) a plurality of scanners and data collection methods used to capture thermographic and photogrammetric imagery of a subject animal positioned in a target area and a subject animal in motion through the target area of a scanning enclosure, wherein the captured thermographic and photogrammetric imagery is supplemented by additional heterogeneous information obtained from the subject animal and aggregated together for classification of all the heterogeneous information, wherein the classified heterogeneous information is further evaluated by at least one subject matter expert (SME) who provides a ranking determination and a rating determination as to any conditions or health indicators present in the subject animal, (ii) an artificial intelligence (AI) neural network that is used to support and provide a diagnosis of the subject animal, (iii) an AI expert system that is trained to provide a diagnosis based on ranking determinations, rating determinations, conditions, and health indicators provided by one or more SMEs, (iv) an AI digital library deep learning module in which all the collected data is added for use by the AI expert system, (v) a diagnosis and audit trail module that provides health diagnoses of the subject animal with an audit trail on parameters involved in determining diagnoses, and (vi) a treatment and reference module that provide treatment and reference information regarding the health diagnoses of the subject animal, wherein the treatment and reference information is fed back to the expert system for processing the scans of other animals. In some embodiments, the animal health, performance, fitness, training regimen, and breeding potential assessment system uses an AI expert system with deep learning analysis to analyze health history of an animal, performance of the animal, and breeding potential of the animal. This approach provides a highly accurate, repeatable and unbiased method to evaluate an animal and to recommend diagnosis and treatment. In some embodiments, the animal health, performance, fitness, training regimen, and breeding potential assessment system includes a consultation aggregation and presentation module that generates consultation materials with infographics, video, diagnosis, prescriptions, imaging results, laboratory results, racing history, training history, health history, treatment options, rehabilitation markers, prognosis and follow up recommendations. In some embodiments, the consultation aggregation and presentation module provides consultation materials first manually from the results, and then provides a second set of comparable consultation materials using an AI expert system. In some embodiments, the animal health, performance, fitness, training regimen, and breeding potential assessment system further includes a real-time data provisioning engine that provides the captured thermographic and photogrammetric imagery, the additional aggregated and classified heterogeneous information obtained from the subject animal, and other information about the subject animal to external devices in real-time. In some embodiments, the external devices include augmented reality goggles to provide augmented views generated in real-time in order to provide enhanced views of the subject animal for on-site viewing by a SME.

In some embodiments, the method for diagnosing, determining treatment, and determining prognosis of health, performance, fitness, training regimen, and breeding condition of an animal subject using expert systems, data integration, imaging and 3D scanning technology includes a plurality of steps comprising (i) a subject animal entering a target area in a scanning system enclosure, (ii) the subject animal being positioned for scan (optionally on pressure mat), (iii) waiting for the subject animal to maintain a steady pose for a threshold time duration (e.g., one second) while scanners perform thermographic and photogrammetric scans, optical cameras or motion sensors track motion, and force plates or pressure mats weigh the animal and determines posture, alignment, inflammation, and balance of the subject animal, (iv) the subject animal walks through the scanning area at a fixed pace while the scanners perform thermographic and photogrammetric scans, optical cameras or motion sensors track motion, force plates or pressure mat analyze step placement and determines posture, inflammation, and gait, (v) performing optional laboratory work as needed and providing real-time data to devices such as augmented reality goggles to provide augmented views generated in real-time, thereby providing enhanced views for on-site viewing by a subject matter expert (SME), such as a breeder, a trainer, a veterinarian, etc., (vi) aggregating and organizing the information from the scanners, motion sensors, force plates, pressure mat, and optional lab work, (vii) generating layered representations of the information, and thereby allow the subject animal to be viewed in multiple different perspectives (e.g., skeletal, thermal, surface, body measurement, and optical), (viii) training the expert system via SME inputs (initialize and train new expert system or update/retrain existing expert system), (ix) feeding the aggregated and organized data to the expert system, and (x) providing diagnosis of condition(s), reference information regarding the condition(s), and treatment information for the condition(s). In some embodiments, the method for diagnosing, determining treatment, and determining prognosis of health, performance, fitness, training regimen, and breeding condition of an animal subject using expert systems, data integration, imaging and 3D scanning technology extracts deep learning analysis results from an AI expert system to analyze health history of an animal, performance of the animal, and breeding potential of the animal.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

In this specification, reference is made to an animal subject (or subject animal) which is often exemplified as a horse. However, for purposes of this disclosure, such animal subject is not limited to only a horse or any other particular animal. Instead, the animal subject referred to throughout this description broadly refers to any animal subject to which a user wishes to evaluate health, performance, fitness, training regimen, breeding potential, or other aspects. Thus, the term animal subject (or subject animal) is broad enough to include a human subject, such as a professional athlete to track the effects of training and competition on the body of the athlete. Other animals are also anticipated, such as bovine animals (e.g., cows), ostriches, tigers, giraffes, elephants, or other domestic animals, exotic animals, or zoo animals.

Some embodiments of the invention include a novel animal health, performance, fitness, training regimen, and breeding potential assessment system and a novel method for diagnosing, determining treatment, and determining prognosis of health, performance, fitness, training regimen, and breeding condition of an animal subject using expert systems, data integration, imaging and 3D scanning technology. In some embodiments, the animal subject is a horse. In some embodiments, the animal subject is a human. In some embodiments, the animal subject is a bovine animal. In some embodiments, the animal subject is an ostrich. In some embodiments, the animal subject is a non-domesticated exotic animal. Examples of non-domesticated exotic animals include, without limitation, tigers, elephants, giraffes, rhinoceroses, non-human apes, zebras, birds, bats, wolverines, lions, panthers, badgers, and any of the many kinds of exotic animals which can be seen in zoos or which roam wildly in nature. In some embodiments, the animal health, performance, fitness, training regimen, and breeding potential assessment system and the method for diagnosing, determining treatment, and determining prognosis of health, performance, fitness, training regimen, and breeding condition of an animal subject utilize expert systems, data integration, imaging and 3D scanning technology, and other methods, systems, and/or technology to collect data in a very precise and repeatable manner. In some embodiments, the animal health, performance, fitness, training regimen, and breeding potential assessment system is a scalable system that accommodates different sizes of different animal subjects. In this way, the animal health, performance, fitness, training regimen, and breeding potential assessment system is capable of scaling the scanning system in a way that covers a range of sizes of the animal subject, thereby allowing for scanning of very small animal subjects, such as rodents, cats, dogs, badgers, etc., very large animal subjects, such as giraffes and elephants, and everything in between, such as ostriches, cows, horses, humans, non-human apes, tigers, lions, panthers, other big wild cats, etc.

In some embodiments, the animal health, performance, fitness, training regimen, and breeding potential assessment system includes (i) a plurality of scanners and data collection methods used to capture thermographic and photogrammetric imagery of a subject animal positioned in a target area of a scanning enclosure, wherein the captured thermographic and photogrammetric imagery is supplemented by additional heterogeneous information obtained from the subject animal and aggregated together for classification of all the heterogeneous information, wherein the classified heterogeneous information is further evaluated by at least one subject matter expert (SME) who provides a ranking determination and a rating determination as to any conditions or health indicators present in the subject animal, (ii) an artificial intelligence (AI) neural network that is used to support and provide a diagnosis of the subject animal, (iii) an AI expert system that is trained to provide a diagnosis based on ranking determinations, rating determinations, conditions, and health indicators provided by one or more SMEs, (iv) an AI digital library deep learning module in which all the collected data is added for use by the AI expert system, (v) a diagnosis and audit trail module that provides health diagnoses of the subject animal with an audit trail on parameters involved in determining diagnoses, and (vi) a treatment and reference module that provide treatment and reference information regarding the health diagnoses of the subject animal, wherein the treatment and reference information is fed back to the expert system for processing the scans of other animals. In some embodiments, the animal health, performance, fitness, training regimen, and breeding potential assessment system uses an AI expert system with deep learning analysis to analyze health history of an animal, performance of the animal, and breeding potential of the animal. This approach provides a highly accurate, repeatable and unbiased method to evaluate an animal and to recommend diagnosis and treatment. In some embodiments, the animal health, performance, fitness, training regimen, and breeding potential assessment system includes a consultation aggregation and presentation module that generates consultation materials with infographics, video, diagnosis, prescriptions, imaging results, laboratory results, racing history, training history, health history, treatment options, rehabilitation markers, prognosis and follow up recommendations. In some embodiments, the consultation aggregation and presentation module provides consultation materials first manually from the results, and then provides a second set of comparable consultation materials using the AI expert system. In some embodiments, the animal health, performance, fitness, training regimen, and breeding potential assessment system further includes a real-time data provisioning engine that provides the captured thermographic and photogrammetric imagery, the additional aggregated and classified heterogeneous information obtained from the subject animal, and other information about the subject animal to external devices in real-time. In some embodiments, the external devices include augmented reality goggles to provide augmented views generated in real-time in order to provide enhanced views of the subject animal for on-site viewing by a SME.

In some embodiments, the method for diagnosing, determining treatment, and determining prognosis of health, performance, fitness, training regimen, and breeding condition of an animal subject using expert systems, data integration, imaging and 3D scanning technology includes a plurality of steps comprising (i) a subject animal entering a target area in a scanning system enclosure, (ii) the subject animal being positioned for scan (optionally on pressure mat), (iii) waiting for the subject animal to maintain a steady pose for a threshold time duration (e.g., one second) while scanners perform thermographic and photogrammetric scans, optical cameras or motion sensors track motion, and force plates or pressure mat weighs the animal and determines posture, alignment, inflammation, and balance of the subject animal, (iv) the subject animal walks through the scanning area at a fixed pace while the scanners perform thermographic and photogrammetric scans, optical cameras or motion sensors track motion, force plates or pressure mat analyze step placement and determines posture, inflammation, and gait, (v) performing optional laboratory work as needed and providing real-time data to devices such as augmented reality goggles to provide augmented views generated in real-time, thereby providing enhanced views for on-site viewing by a subject matter expert (SME), such as a breeder, a trainer, a veterinarian, etc., (vi) aggregating and organizing the information from the scanners, motion sensors, force plates, pressure mat, and optional lab work, (vii) generating layered representations of the information, and thereby allow the subject animal to be viewed in multiple different perspectives (e.g., skeletal, thermal, surface, body measurement, and optical), (viii) training the expert system via SME inputs (initialize and train new expert system or update/retrain existing expert system), (ix) feeding the aggregated and organized data to the expert system, and (x) providing diagnosis of condition(s), reference information regarding the condition(s), and treatment information for the condition(s). In some embodiments, the method for diagnosing, determining treatment, and determining prognosis of health, performance, fitness, training regimen, and breeding condition of an animal subject using expert systems, data integration, imaging and 3D scanning technology extracts deep learning analysis results from an AI expert system to analyze health history of an animal, performance of the animal, and breeding potential of the animal.

As stated above, animals, such as horses, are used for sport and are often bred and conditioned to race and perform in one or more sports. Currently, there is no existing method or process to consistently and independently evaluate and diagnose an animal's health, performance, and breeding potential. Conventionally, the present method for assessing a horse's health is by visual inspection from a trainer, an owner, a breeder, or a veterinarian. As such, determinations of fitness for breeding, state of conditioning, and whether to purchase animals, especially horses, are presently subjective and rely on the expertise and opinions of trainers, veterinarians, owners, or others. The assessments of different evaluators can therefore vary because the nature of the conventional method is highly subjective and can be easily influenced by competing business and personal objectives. Embodiments of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology described in this specification solve such problems by scanning and analyzing physical parameters of an animal, such as a horse, using photogrammetry, thermography, force plates, laboratory tests, medical and veterinary records, motion tracking, and other methods to quickly gather heterogeneous information (also referred to simply as "data") about the animal. The heterogeneous information is aggregated and classified into an expert system with deep learning analysis and optional block chain tracking, to diagnose the animal's health, performance, and breeding potential. By employing an approach that uses Artificial Intelligence (AI), embodiments of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology provide highly accurate, repeatable, and unbiased ways to evaluate animals for owners, buyers, insurers, breeders, veterinarians, and other interested users.

Embodiments of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology described in this specification differ from and improve upon currently existing options. In particular, some embodiments differ by utilizing data integration, imaging and 3D scanning technology, and other objective methods, systems, and technology to collect data in a highly exacting, personalized, and repeatable manner in which scanning flexibility is extended to any of several animal subjects (e.g., domesticated animals, exotic animals, humans, very large animal subjects, very small animal subjects, etc.) and the measurements resulting from scanning of any animal subject can be used for any of several different purposes or goals, such as detection of injury or pregnancy, evaluation of general health, etc. For example, monitoring pregnancy is very important for bovine farmers and zoos, while evaluation and detection of injury is important for human athletes and horse owners and trainers. In particular, the animal health, performance, fitness, training regimen, and breeding potential assessment system includes an AI expert system with deep learning analysis that is employed to diagnose the animal's history, health, performance, and breeding potential. This approach provides a highly accurate, repeatable and unbiased method to evaluate an animal. Since the animal health, performance, fitness, training regimen, and breeding potential assessment system does not involve harmful radiation, or require sedation or restraints of an animal subject, the purposes and goals for usage of the animal health, performance, fitness, training regimen, and breeding potential assessment system are virtually unlimited.

Embodiments of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology described in this specification use data integration, imaging and 3D scanning technology and other methods to collect data in a very precise and repeatable process, which avoids bias that may be inherent in evaluation of any subject matter expert (SME), such as a horse breeder, trainer, veterinarian, etc. Furthermore, the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology of the present disclosure employs artificial intelligence algorithms and deployed AI systems (i.e., the AI expert system) with deep learning analysis to analyze health history of the animal being scanned and evaluated, as well as potential performance of the subject animal, and/or breeding potential of the animal. This approach provides a highly accurate, repeatable and unbiased method (objective method) to evaluate an animal and to recommend diagnosis and treatment.

In addition, embodiments of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology improve upon the currently existing options, which include subjective human evaluation. Human inspections of animals vary widely. For instance, human inspections of a horse can be completed by any of several highly trained and skilled professionals, such as a very experienced horse trainer, a recognized expert horse breeder, or a highly experienced veterinarian; yet all of these highly respected and knowledgeable experts can perform analysis of a horse and formulate different health assessments for the horse due to any of several factors that introduce subjective, human-related ambiguity into the analysis, such as having competing interests, having different experiences and knowledge backgrounds, having varied training, and taking different perspectives as to the analysis, such as a perspective biased towards racing objectives versus a perspective biased towards breeding objectives. By contrast, the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology utilize and rely on unbiased, objective aspects of data integration, imaging and 3D scanning technology, and other methods, systems, and technology in the collection and analysis of data, in a way that does not deviate in objective data collection and analysis no matter how many times repeated. It is also possible to use the animal health, performance, fitness, training regimen, and breeding potential assessment system to evaluate the effect of the training regimen to determine whether the training regimen of the subject animal is working as expected or should be modified in one way or another. For example, it is possible to weigh the effects of the training regimen on the subject animal (e.g., horse training, greyhound race training, or a human athlete's training regimen) by scanning the subject animal before training and then again after training and comparing the results afterwards.

Additionally, the method for diagnosing, determining treatment, and determining prognosis of health, performance, fitness, training regimen, and breeding condition of an animal subject using expert systems, data integration, imaging and 3D scanning technology extracts objective data derived from the deep learning analysis performed by the AI expert system, and based on this data, is able to analyze the an animal's history health, performance, and breeding potential in a way that is highly accurate, repeatable, and unbiased for any number of different animals evaluated.

The animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology of the present disclosure may be comprised of the following elements. This list of possible constituent elements is intended to be exemplary only and it is not intended that this list be used to limit the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology of the present application to just these elements. Persons having ordinary skill in the art relevant to the present disclosure may understand there to be equivalent elements that may be substituted within the present disclosure without changing the essential function or operation of the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology.

1. Scanners and Data Collections methods for scanning and analyzing physical parameters of a subject animal, such as a horse, using photogrammetry, thermography, force plates (pressure plates), lab work, motion tracking and other methods to quickly gather data about the subject animal. Scanners includes a variety of cameras and sensors that are disposed along posts of varying lengths and sizes, such that the animal health, performance, fitness, training regimen, and breeding potential assessment system can be scaled to accommodate different sizes of different animal subjects (e.g., scaled up for very large animals, scaled down for very small animals, etc.).

2. Aggregated and Classified data includes heterogeneous information that is aggregated and classified.

3. Expert system with Deep Learning using artificial intelligence (AI) and input/feedback of experts (to train the system), as well as expert input searches to determine the health indicators.

4. Diagnosis (DX) with Audit Trail. The system will provide health diagnosis with an audit trail on what parameters determine the diagnosis.

5. Treatment (RX) and references for the diagnosis conditions will be feedback into the system for future scans.

6. Artificial Intelligence (AI) Digital Library Deep Learning. In some embodiments, all collected data will be added to the AI Digital Deep Learning Library.

7. Artificial Intelligence (AI) Neural Network. The AI neural network is a deep learning neural network that is created to support the diagnosis.

8. Expertise Ranking and Rating to provide for objective, consistent analysis that supports objective ranking and rating of subject animals. In some embodiments, an expert evaluator, such as a veterinarian, a trainer, or a breeder, reviews the data and provides ranking and rating determinations about conditions and health indicators, which is used to train the system.

9. Generation of consultation with infographics, video, diagnosis, prescriptions, imaging results, laboratory results, racing history, training history, health history, treatment options, rehabilitation markers, prognosis and follow up recommendations.

Figure 1:
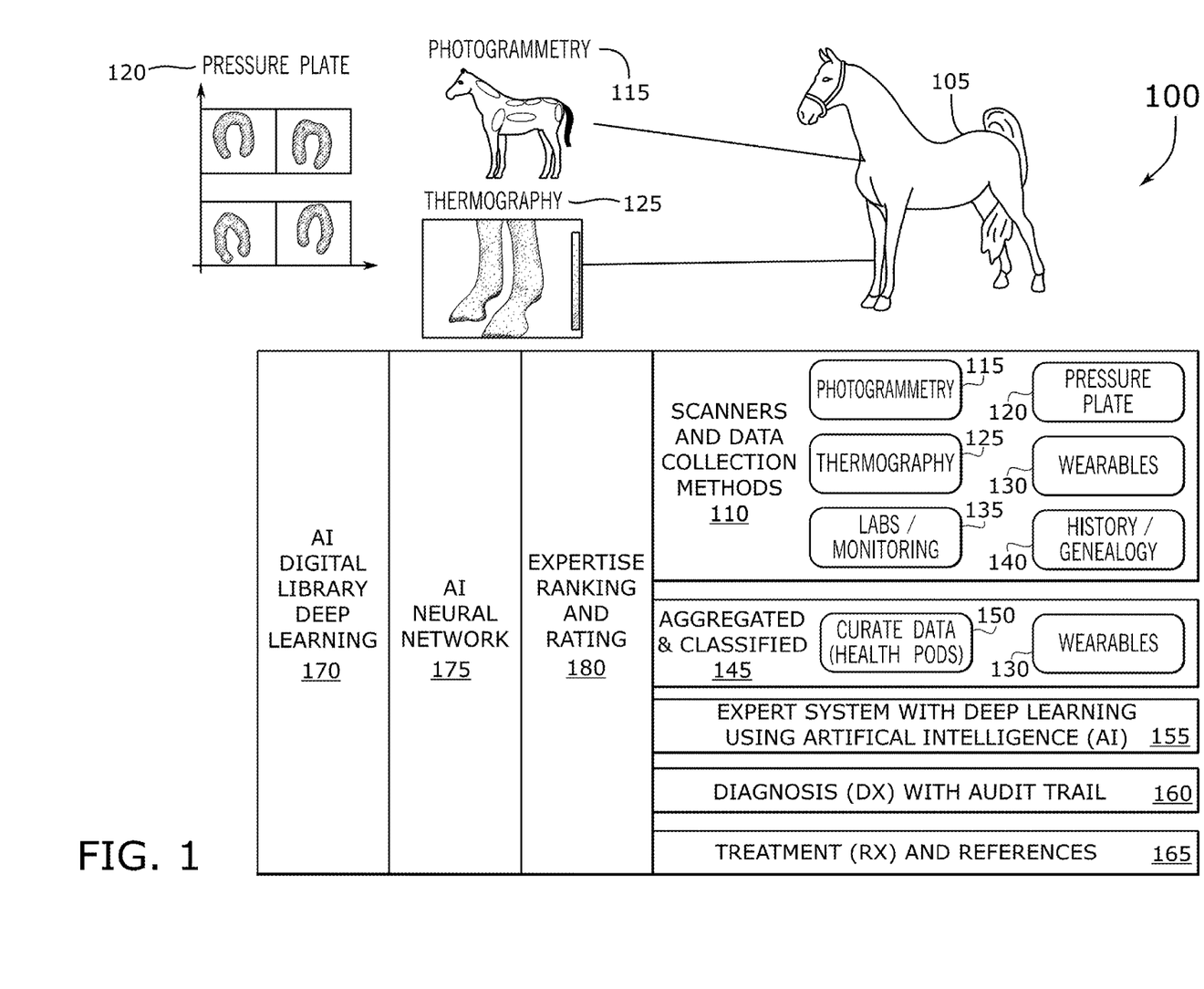
FIG. 1 conceptually illustrates a block diagram of an animal health, performance, fitness, training regimen, and breeding potential assessment system that is used to perform a method for diagnosing, determining treatment, and determining prognosis of health, performance, fitness, training regimen, and breeding condition of an animal subject using expert systems, data integration, imaging and 3D scanning technology in some embodiments.

By way of example, FIG. 1 conceptually illustrates a block diagram of an animal health, performance, fitness, training regimen, and breeding potential assessment system 100 that is used to perform a method for diagnosing, determining treatment, and determining prognosis of health, performance, fitness, training regimen, and breeding condition of an animal subject using expert systems, data integration, imaging and 3D scanning technology in some embodiments. As shown in this figure, the animal health, performance, fitness, training regimen, and breeding potential assessment system 100 is used to scan and assess a horse 105 for health, performance, fitness, and/or breeding potential. To do so, the animal health, performance, fitness, training regimen, and breeding potential assessment system 100 includes a plurality of scanners and data collection methods 110, including photogrammetry 115, a pressure plate 120, thermography 125, one or more wearable devices 130, labs/monitoring 135 work, and history/genealogy 140 aspects. Thus, for example, the photogrammetry 115 allows the horse 105 to captured by a plurality of cameras, the pressure plate 120 can weigh the horse 105 and identify problems with the stance of the horse 105 or gait of the horse 105 while standing (e.g., checking if the horse 105 favors some legs over another leg), and can identify other ailments based on temperature data from thermography 125.

Additionally, the animal health, performance, fitness, training regimen, and breeding potential assessment system 100 includes aggregated and classified modules 145 for the data obtained when scanning of the horse 105 is obtained. The aggregated and classified modules 145 include one to curate data (health pods) 150 and other wearable devices 130. Furthermore, the animal health, performance, fitness, training regimen, and breeding potential assessment system 100 includes an expert system with deep learning using artificial intelligence (AI) 155.

In some embodiments, the animal health, performance, fitness, training regimen, and breeding potential assessment system 100 is able to produce a diagnosis (DX) with an audit trail 160 based on the aggregated and classified 145 data captured by the scanners and data collection methods 110 when performing the scan of the horse 105. In some embodiments, the animal health, performance, fitness, training regimen, and breeding potential assessment system 100 is able to determine a treatment (RX) and references 165 after the DX with audit trail 160.

In some embodiments, the animal health, performance, fitness, training regimen, and breeding potential assessment system 100 further includes AI digital library deep learning 170, an AI neural network 175, and performs expertise ranking and rating 180 of the horse 105, which is both objective and consistent across different horses or animals and from scan to scan.

The animal health, performance, fitness, training regimen, and breeding potential assessment system 100 that is used to perform a method for diagnosing, determining treatment, and determining prognosis of health, performance, fitness, training regimen, and breeding condition of an animal subject using expert systems, data integration, imaging and 3D scanning technology would (typically) be used by owners, insurers, breeders, and veterinarians to scan and diagnosis horses (or other animals, as needed) to evaluate the horse's health, market value, treatment results, and fitness to race.

In some embodiments, the method for diagnosing, determining treatment, and determining prognosis of health, performance, fitness, training regimen, and breeding condition of an animal subject using expert systems, data integration, imaging and 3D scanning technology of the present disclosure may be comprised of the following steps. Persons having ordinary skill in the art relevant to the present disclosure may understand there to be equivalent steps that may be substituted within the present disclosure without changing the essential function or operation of the method for diagnosing, determining treatment, and determining prognosis of health, performance, fitness, training regimen, and breeding condition of an animal subject using expert systems, data integration, imaging and 3D scanning technology.

1. Animal enters target area in scanning system enclosure. (Scaling of the posts with scanners/cameras/sensors is either a step prior to the animal entering the target area or can be performed contemporaneously.)

2. Animal positioned for scan (optionally on pressure mat).

3. Animal maintains steady pose for threshold time duration (e.g., one second) while scanners perform thermographic and photogrammetric scans, motion sensors track motion, and force plates or pressure mats weigh the animal and determines alignment, inflammation, posture, and balance of the animal.

4. Animal walks through scanning system enclosure at a steady pace while the scanners perform thermographic and photogrammetric scans, optical motion sensors (or motion sensors) track motion, and force plates or pressure mats assess steps and determines gait, alignment, inflammation, and balance of the animal.

5. Optional laboratory work is performed as needed. Optional augmented views generated in real-time allow for on-site viewing by a subject matter expert (SME), such as a breeder, a trainer, a veterinarian, etc.

6. Information from the scanners, motion sensors, force plates, pressure mat, and optional lab work is aggregated and organized to generate layered representations of the information, and thereby allow the animal to be viewed in multiple different perspectives (e.g., skeletal, thermal, surface, body measurement, and optical).

7. Train the expert system via subject matter expert (SME) inputs (initialize and train new expert system or update/retrain existing expert system).

8. Generate and provide consultation discussing diagnosis, laboratory, and imaging results, treatment options, prognosis, and rehabilitation plans.

9. Feed the aggregated and organized data to the expert system.

10. Provide diagnosis of condition(s), reference information regarding the condition(s), and treatment information for the condition(s).

Figure 2:
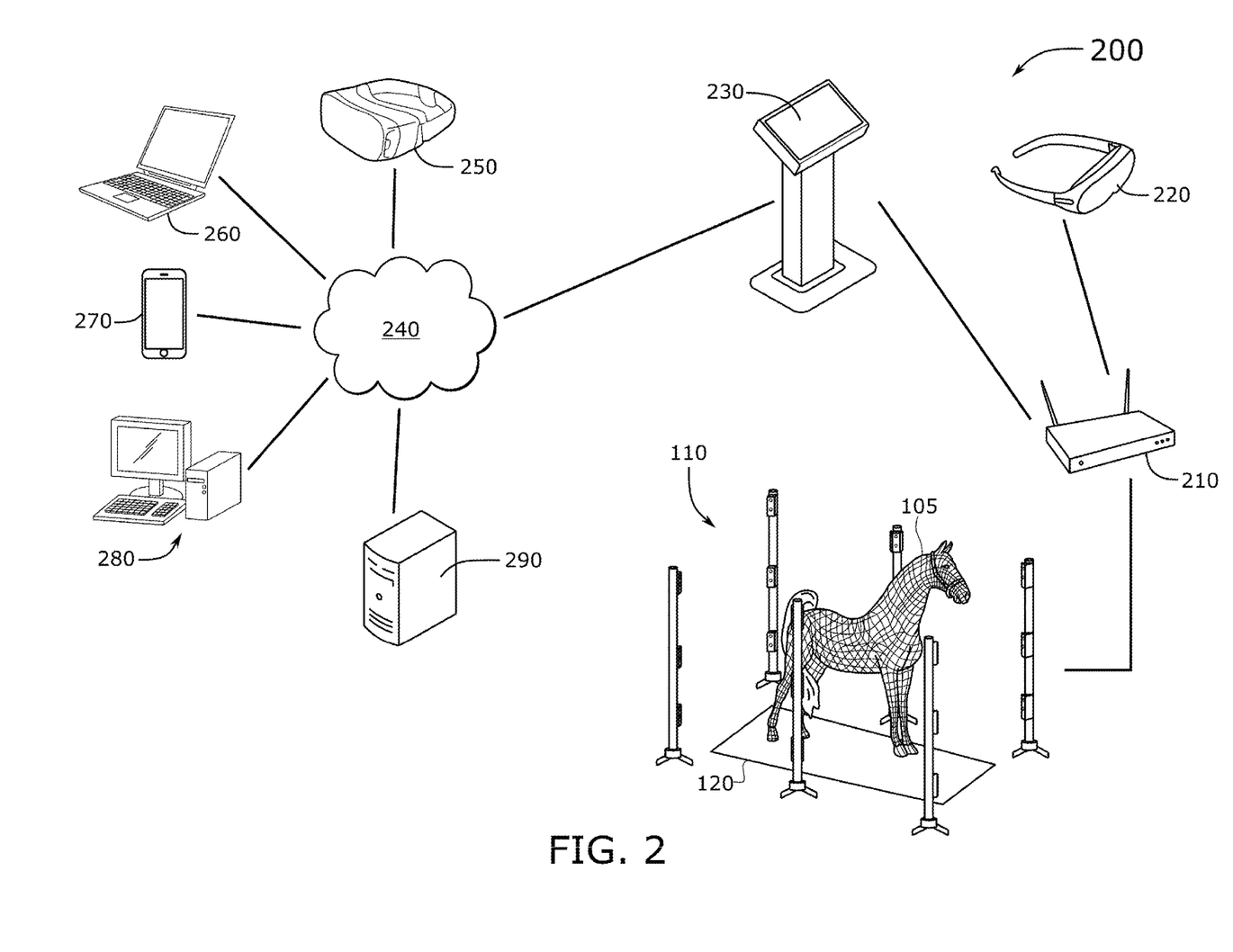
FIG. 2 conceptually illustrates a network architecture of an animal health, performance, fitness, training regimen, and breeding potential assessment system when performing the method for diagnosing, determining treatment, and determining prognosis of health, performance, fitness, training regimen, and breeding condition of an animal subject using expert systems, data integration, imaging and 3D scanning technology in some embodiments.

By way of example, FIG. 2 conceptually illustrates a network architecture of an animal health, performance, fitness, training regimen, and breeding potential assessment system when performing the method for diagnosing, determining treatment, and determining prognosis of health, performance, fitness, training regimen, and breeding condition of an animal subject using expert systems, data integration, imaging and 3D scanning technology 200. In particular, the method for diagnosing, determining treatment, and determining prognosis of health, performance, fitness, training regimen, and breeding condition of an animal subject using expert systems, data integration, imaging and 3D scanning technology 200 works in connection with the animal health, performance, fitness, training regimen, and breeding potential assessment system 100. An example of this shown in FIG. 2, with steps of the method for diagnosing, determining treatment, and determining prognosis of health, performance, fitness, training regimen, and breeding condition of an animal subject using expert systems, data integration, imaging and 3D scanning technology 200 demonstrated over a network.

First, a scanning system with scanners and data collection methods 110 are used to scan the horse 105 stationed on the pressure plate 120. The scanning system is shown in this figure in a partial setup with several cameras on posts surrounding the horse 105. Second, the horse 105 (or any other animal being used as the subject), is directed to or allowed to enter a target area within the scanning system— which in this figure includes the pressure plate 120. In some cases, the target area of the scanning system could be deployed without a pressure plate. The scanning system would deploy with multiple scanning devices, typically cameras and other sensor-type devices. As shown in this figure, the scanning system has multiple cameras on posts around the target area (around the horse 105). In some embodiments, the animal health, performance, fitness, training regimen, and breeding potential assessment system 100 includes multiple RGB cameras with depth sensors and thermal cameras mounted to provide complete 3D mapping of the subject animal. A more detailed example of the animal health, performance, fitness, training regimen, and breeding potential assessment system with multiple cameras around a target area is described below, by reference to FIG. 3.

In some embodiments, the subject animal is scanned in static pose and in motion. The subject animal is required to maintain a pose for a time duration that allows for the scanning system to perform its scanning and imaging processes. For example, maintaining a static pose for one second may be sufficient. The subject animal is required to maintain a steady pace and pass through the scanning system to perform its scanning and imaging processes. In FIG. 2, the animal health, performance, fitness, training regimen, and breeding potential assessment system 100 may not be able to complete a full scan of the horse 105 unless/until the horse 105 maintains a pose for the threshold duration of time. For example, the subject animal (the horse 105) may be required to maintain a standing pose and be still for one second. Given these constraints (subject animal in target area and remaining still for duration of time), the third step includes scanning and imaging of the subject animal (the horse 105) by the animal health, performance, fitness, training regimen, and breeding potential assessment system 100. In some embodiments, a pressure mat 120 is included in the target area and the subject animal (the horse 105) is positioned to stand on the mat 120 in the target area. While not required, in some embodiments, the pressure mat 120 measures how the subject animal is standing. In some embodiments, the pressure mat 120 also acts as a scale by which the subject animal is weighed while standing on the mat. In some embodiments, the scanning and imaging is repeated multiple times, depending on the needs and requirements of the user. In some embodiments, the scanning step also includes laboratory work.

Also in reference to FIG. 2, the animal health, performance, fitness, training regimen, and breeding potential assessment system 100 may not be able to complete a full scan of the horse 105 unless/until the horse 105 manages to move at a steady pace through the scanning system. For example, the subject animal (the horse 105) may be required to maintain a steady pace while moving through the entire length of the scanning area. Given these constraints (subject animal maintaining a steady pace while moving through the scanning area), this step includes scanning and imaging of the subject animal (the horse 105) by the animal health, performance, fitness, training regimen, and breeding potential assessment system 100. In some embodiments, a pressure mat 120 is included in the stride placement (the horse 105) on the mat 120 in the target area. In some embodiments, the scanning and imaging is repeated multiple times, depending on the needs and requirements of the user. As above, this step may also include laboratory work in some embodiments.

After the subject animal is scanned, the information is aggregated and the data is organized as follows. A detailed point cloud is created and a markerless measurement method is used to establish body markers. An example of a detailed point cloud is described below, by reference to FIG. 3.

Figure 4:
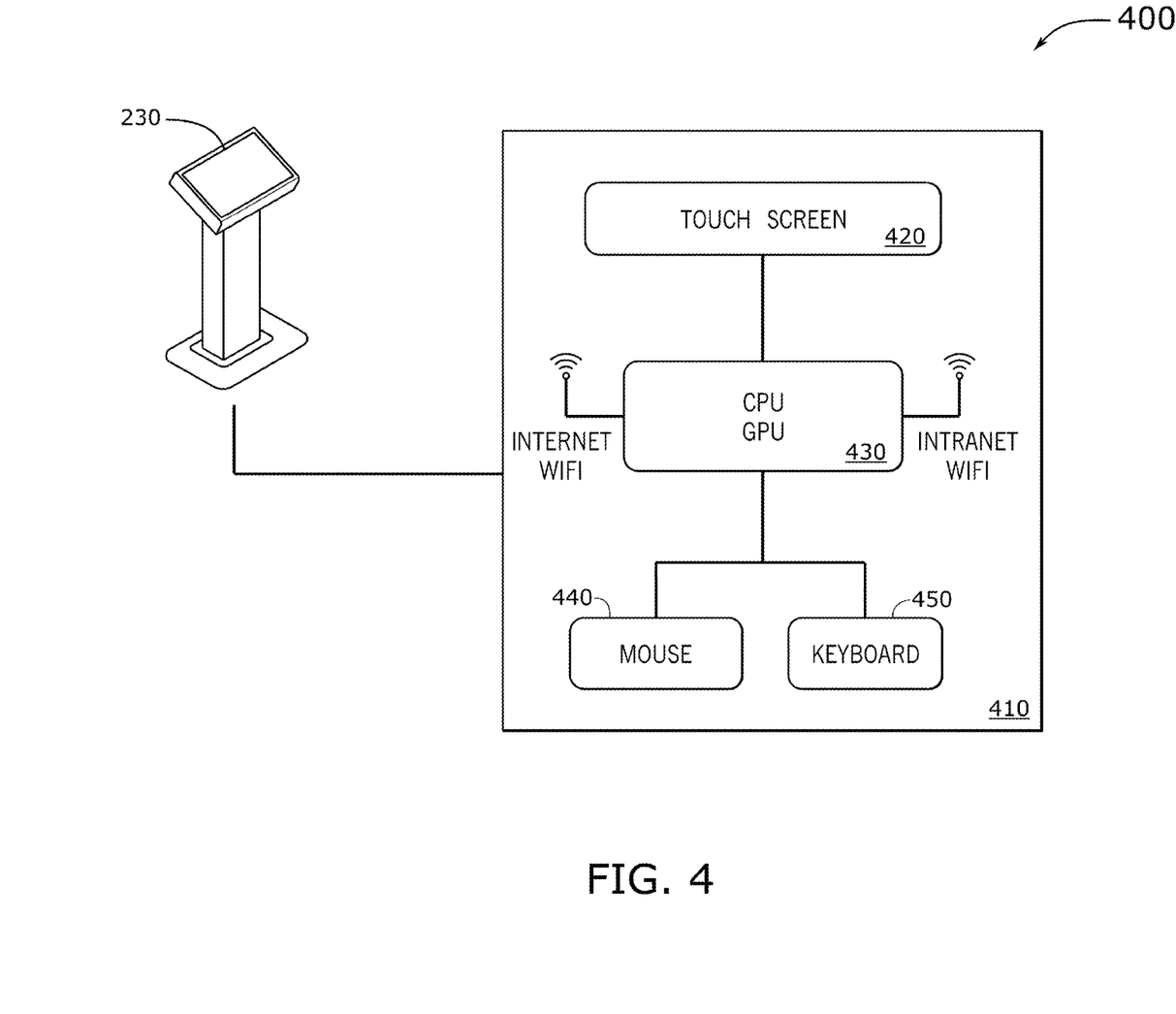
FIG. 4 conceptually illustrates an internal scanner control computing device of a scanner control station used in an animal health, performance, fitness, training regimen, and breeding potential assessment system of some embodiments.

Referring back to FIG. 2, after the subject animal (the horse 105) has been scanned, the aggregated and classified data from the scan is transmitted by a secure high-speed internet wireless router 210 to a scanner control station 230. A more detailed example of a scanner control station 230 is described below, by reference to FIG. 4. In some embodiments, the secure high-speed internet wireless router 210 transmits the horse 105 scan information to an augmented reality headset 220 of a trainer, breeder, veterinarian, or other interested user in real-time. The user of the augmented reality headset 220 can then view the horse 105 with augmented overlays of scan data pertaining to the health, temperature, weight, constitution, or other aspects related to the horse 105. In this way, the augmented reality headset 220 is an excellent device that seamlessly works with the animal health, performance, fitness, training regimen, and breeding potential assessment system 100 for the purpose of diagnosing, determining treatment, and determining prognosis of health, performance, fitness, training regimen, and breeding condition of the horse 105, or any other subject animal (including a human athlete or other human subject, for example), using expert systems, data integration, imaging and 3D scanning technology of the animal health, performance, fitness, training regimen, and breeding potential assessment system 100.

In some embodiments, the scanner control station 230 is able to distribute the scanned data, the diagnosis, the treatment recommendation, etc., to a plurality of networked devices over the Internet 240. In some embodiments, the plurality of networked devices seamlessly integrate with the animal health, performance, fitness, training regimen, and breeding potential assessment system 100 to view scan data of the subject animal. In some embodiments, the plurality of networked devices include one or more of any of the following devices: a virtual reality headset 250, a laptop computer 260, a mobile device/tablet computing device 270, a desktop computer 280 and a hosted AI diagnosis server 290.

Scanning the subject animal (the horse 105) occurs after the animal is positioned within the target area. Further processing of the data occurs after scanning of the subject animal is completed.

Figure 3:
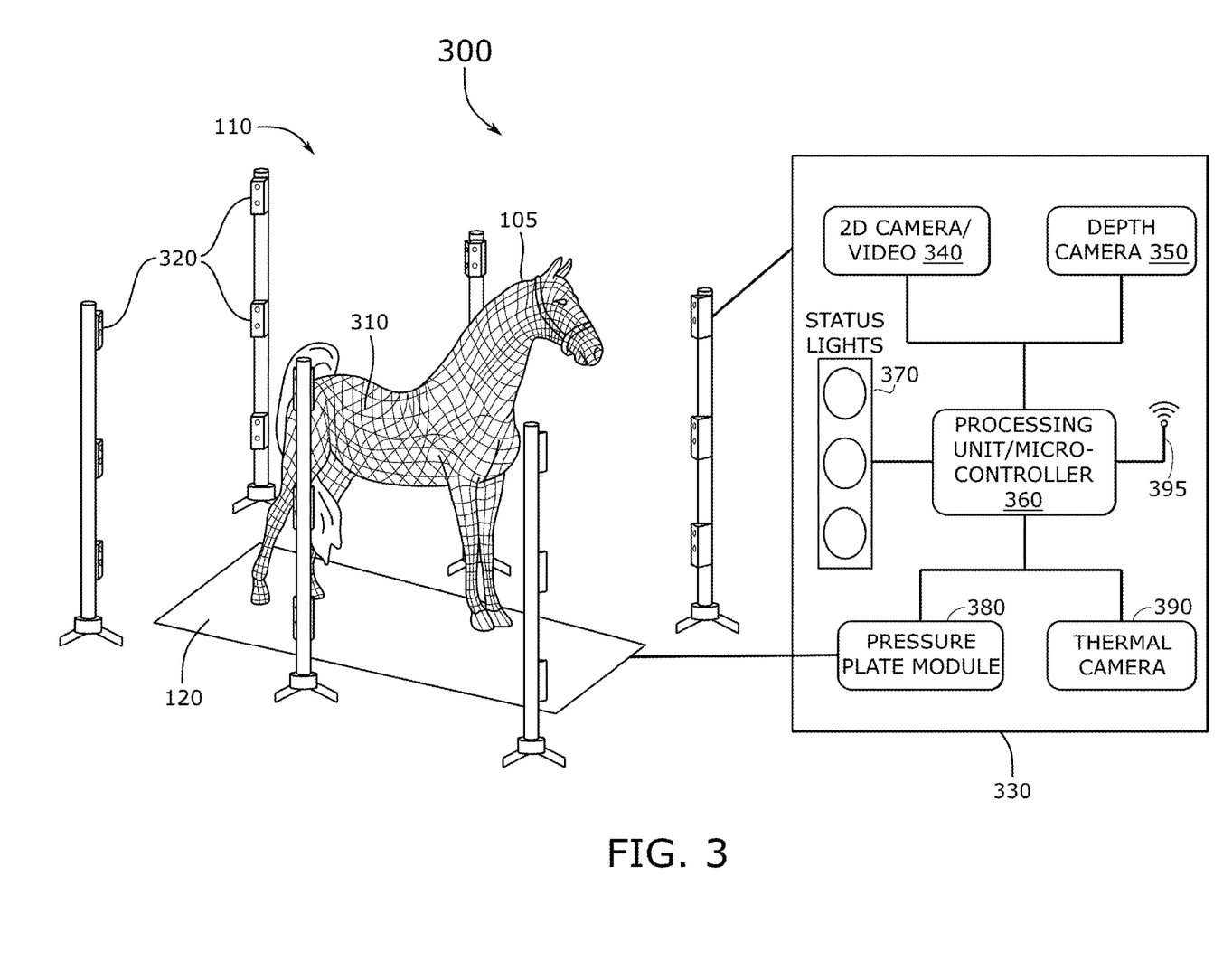
FIG. 3 conceptually illustrates a scanner box of an animal health, performance, fitness, training regimen, and breeding potential assessment system that is used to aggregate and classify data from the scanners and data collection methods conducted during the method for diagnosing, determining treatment, and determining prognosis of health, performance, fitness, training regimen, and breeding condition of an animal subject using expert systems, data integration, imaging and 3D scanning technology in some embodiments.

By way of example, FIG. 3 conceptually illustrates a scanner box of an animal health, performance, fitness, training regimen, and breeding potential assessment system that is used to aggregate and classify data from the scanners and data collection methods conducted during the method for diagnosing, determining treatment, and determining prognosis of health, performance, fitness, training regimen, and breeding condition of an animal subject using expert systems, data integration, imaging and 3D scanning technology 300. As shown in this figure, the scanners and data collection methods 110 are performed when the horse 105 is positioned in the target area. In this figure, the horse 105 is standing on the pressure mat 120. The horse 105 maintains a pose for the threshold duration of time, a plurality of cameras 320, which are disposed along several posts that surround the target area, performing photogrammetry 115 imaging, thermography 125 imaging, etc., to capture several sets of image and sensor-based scan data. The image and sensor-based data from the plurality of cameras 320 is transmitted to (or retrieved by) a scanner box 330. In some embodiments, the scanner box 330 is a custom computing device with computing device modules able to process the image and sensor-based data from the plurality of cameras 320. In some embodiments, the scanner box 330 includes a two-dimensional ("2D") camera/video unit 340, a depth camera unit 350 that allows for 3D imagery to be created from 2D images, a processing unit/micro-controller 360, a plurality of status lights 370, a pressure plate module 380, a thermal camera module 390 (also 2D imaging), and wireless device 395.

After the horse 105 is scanned by the plurality of cameras 320, the information is aggregated and the data is organized as follows. A detailed point cloud 310 is created by the processing unit/micro-controller 360 based on the 2D images and a generated 3D representation from the depth camera 350 information combined with the 2D images. In some embodiments, the detailed point cloud 310 is created and a marker-less measurement method is used to establish body markers. Marker-less measurement entails locating key anatomical features on the animal (the horse 105) and establishing body markers for measurements based on the calculated location in the point cloud 310. Then, using the detailed point cloud 310, the system measures all the relevant body features relative to the body markers which includes but is not limited to the body, limbs, head, hoof, etc. Using the body markers, an animal skeleton is fitted to the reference markers. Next, the skeleton is morphed to fit based on the reference markers. The thermal 2D imaging is mapped to the 3D image using the point cloud 310 information. An exact surface is generated from the point cloud 310 and the RGB colored image is mapped to the surface to create a colorized image. Organizing the data in this sequence enables the system to have a layer representation of the data. The subject animal (the horse 105) can now be viewed in skeleton, thermal, surface, body measurement, and optical views.

In some embodiments, the data from the scanner box 330 is fed to an expert system for further analysis. By way of example, FIG. 4 conceptually illustrates an expert system 400 with an internal scanner control computing device 410 of a scanner control station 230 used in an animal health, performance, fitness, training regimen, and breeding potential assessment system 100. In some embodiments, the internal scanner control computing device 410 includes a touchscreen 420 interface, a CPU/GPU 430, a mouse or other pointing device 440 and a keyboard or other text data input device 450, and is capable of wireless communication over WiFi (i.e., Internet, Intranet, etc.). In some embodiments, the expert system 400 must be trained. This will require the use of subject matter experts (SMEs), such as veterinarians and trainers, to annotate images to identify key health, performance, and breeding issues. Each SME can make the connection between the different data gathered and diagnosis of different conditions. The SME will also provide treatment and references for each of the diagnosis.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 5:
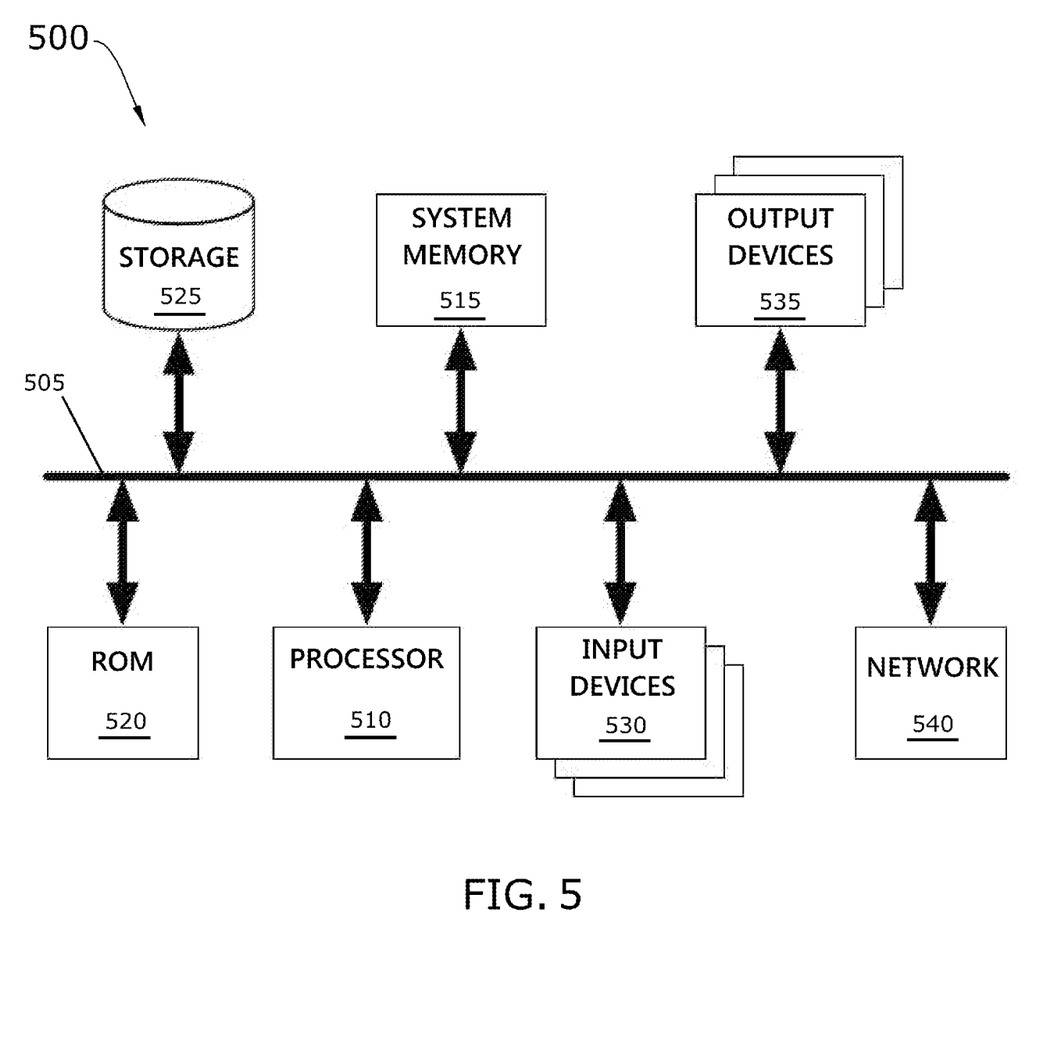
FIG. 5 conceptually illustrates an electronic system with which some embodiments of the invention are implemented.

FIG. 5 conceptually illustrates an electronic system 500 with which some embodiments of the invention are implemented. The electronic system 500 may be a computer, phone (cell phone, mobile phone, smartphone, etc.), PDA (iPod, other handheld computing device, etc.), or any other sort of electronic device or computing device. Such an electronic system includes various types of computer readable media and interfaces for various other types of computer readable media. Electronic system 500 includes a bus 505, processing unit(s) 510, a system memory 515, a read-only 520, a permanent storage device 525, input devices 530, output devices 535, and a network 540.

The bus 505 collectively represents all system, peripheral, and chipset buses that communicatively connect the numerous internal devices of the electronic system 500. For instance, the bus 505 communicatively connects the processing unit(s) 510 with the read-only 520, the system memory 515, and the permanent storage device 525.

From these various memory units, the processing unit(s) 510 retrieves instructions to execute and data to process in order to execute the processes of the invention. The processing unit(s) may be a single processor or a multi-core processor in different embodiments.

The read-only-memory (ROM) 520 stores static data and instructions that are needed by the processing unit(s) 510 and other modules of the electronic system. The permanent storage device 525, on the other hand, is a read-and-write memory device. This device is a non-volatile memory unit that stores instructions and data even when the electronic system 500 is off. Some embodiments of the invention use a mass-storage device (such as a magnetic or optical disk and its corresponding disk drive) as the permanent storage device 525.

Other embodiments use a removable storage device (such as a floppy disk or a flash drive) as the permanent storage device 525. Like the permanent storage device 525, the system memory 515 is a read-and-write memory device. However, unlike storage device 525, the system memory 515 is a volatile read-and-write memory, such as a random access memory. The system memory 515 stores some of the instructions and data that the processor needs at runtime. In some embodiments, the invention's processes are stored in the system memory 515, the permanent storage device 525, and/or the read-only 520. For example, the various memory units include instructions for processing appearance alterations of displayable characters in accordance with some embodiments. From these various memory units, the processing unit(s) 510 retrieves instructions to execute and data to process in order to execute the processes of some embodiments.

The bus 505 also connects to the input and output devices 530 and 535. The input devices enable the user to communicate information and select commands to the electronic system. The input devices 530 include alphanumeric keyboards and pointing devices (also called "cursor control devices"). The output devices 535 display images generated by the electronic system 500. The output devices 535 include printers and display devices, such as cathode ray tubes (CRT) or liquid crystal displays (LCD). Some embodiments include devices such as a touchscreen that functions as both input and output devices.

Finally, as shown in FIG. 5, bus 505 also couples electronic system 500 to a network 540 through a network adapter (not shown). In this manner, the computer can be a part of a network of computers (such as a local area network ("LAN"), a wide area network ("WAN"), or an intranet), or a network of networks (such as the Internet). Any or all components of electronic system 500 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, the animal health, performance, fitness, training regimen, and breeding potential assessment system and the method for diagnosing, determining treatment, and determining prognosis of health, performance, fitness, training regimen, and breeding condition of an animal subject using expert systems, data integration, imaging and 3D scanning technology could be adapted for use in other fields, such as by integration of medical data, imaging and 3D scanning data for diagnosis and treatment of medical conditions in human subjects. Also, the method for diagnosing, determining treatment, and determining prognosis of health, performance, fitness, training regimen, and breeding condition of an animal subject using expert systems, data integration, imaging and 3D scanning technology is described by a series of steps that include specific operations. However, a person of ordinary skill in the relevant art would appreciate that the series of steps of the method is merely an example, and that it may be evident that the steps can be performed in ways other than in the exact order described. Specifically, operations may not be performed in one continuous series of operations, and different specific operations may be performed in different embodiments. Furthermore, the method could be implemented using several sub-processes, or as part of a larger macro process. Thus, one of ordinary skill in the art would understand that the invention is not to be limited by the foregoing illustrative details, but rather is to be defined by the appended claims.

We claim:

1. An animal health, performance, fitness, training regimen, and breeding potential assessment system comprising:
   a plurality of posts surrounding a target area of a scanning enclosure;
   a plurality of scanning devices attached to the plurality of posts and configured to scan a subject animal positioned in the target area and collect diagnostic data related to the subject animal, wherein each scanning device comprises an optical camera configured to capture two-dimensional (2D) images of the subject animal positioned in the target area, a depth sensor configured to detect depth to an anatomical body feature of the subject animal positioned in the target area, and a thermal camera configured to capture thermographic images of the subject animal positioned in the target area of the scanning enclosure, wherein the thermographic images illustrate different colors associated with temperature differences across a plurality of anatomical features of the subject animal;
   a scanner box computing device comprising a microcontroller, a wireless device, and a data storage that stores instructions for (i) receiving 2D images captured by the optical camera of each scanning device, (ii) receiving depth data detected by the depth sensor of each scanning device, (iii) receiving thermographic images captured by the thermal camera of each scanning device, (iv) creating a detailed three-dimensional (3D) point cloud image from the 2D images and depth data, (v) deriving photogrammetric data based on photogrammetric processing of the 2D images and the 3D point cloud image, and (vi) supplementing the thermographic images and photogrammetric data with classified heterogeneous information, wherein the scanner box computing device is communicably connected to the plurality of scanning devices by the wireless device;
   a trained expert system comprising a scanner control station, an artificial intelligence (AI) deep learning neural network, a touchscreen display, and an internal scanner control computing device embedded in the scanner control station, wherein the scanner control computing device comprises a memory storage unit, a WiFi device that communicatively connects the trained expert system to the scanner box computing device, and a processor comprising at least one of a central processing unit and a graphics processing unit, wherein the memory storage unit stores the AI deep learning neural network and instructions for the trained expert system to (i) locate the plurality of anatomical features of the subject animal, (ii) identify a plurality of points in the 3D point cloud image that correspond to the location of each anatomical feature of the subject animal, (iii) establish body marker locations for the plurality of points in the 3D point cloud image for each anatomical feature of the subject animal, (iv) map the thermographic images to the 3D point cloud image, (v) map a colored image to an exterior surface of the 3D point cloud image of the subject animal, and (vi) provide a diagnosis of the subject animal, wherein the memory storage unit stores further instructions for the trained expert system to provide the diagnosis of the subject animal by (vii) detecting, in the thermographic images at any point in the plurality of points of any anatomical feature, elevated temperature that demonstrates inflammation, (viii) evaluating, by comparing body marker locations of each anatomical feature in each pair of corresponding anatomical features of the subject animal, anatomical feature symmetry of the subject animal, and (ix) receiving, from at least one subject matter expert (SME), one or more of ranking determinations, rating determinations, conditions, and health indicators that supplement the diagnosis of the subject animal, wherein the instructions stored in the memory storage unit comprise AI deep learning instructions for supporting, by the AI deep learning neural network, the diagnosis of the subject animal provided by the trained expert system based on a 3D mapping of diagnostic data collected by the plurality of scanning devices to the body marker locations of the 3D point cloud image of the subject animal, wherein the instructions stored in the memory storage unit further comprise instructions to prepare and maintain an audit trail of the diagnosis provided for the subject animal and instructions to provide treatment and reference information including a treatment recommendation based on the diagnosis of the subject animal; and
   a secure high-speed internet wireless router that communicatively connects the trained expert system, the scanner box computing device, and one or more external computing devices in a plurality of networked devices, wherein the scanner control station of the trained expert system connects to the Internet over the secure high-speed internet wireless router, wherein the instructions stored on the memory storage unit of the scanner control computing device comprise instructions to distribute a composite 3D representation of the subject animal, the diagnosis of the subject animal, and the treatment recommendation to the one or more external computing devices in the plurality of networked devices over the Internet, wherein the composite 3D representation of the subject animal comprises the 3D point cloud image of the subject with body markers, the mapped thermographic images, and exterior color applied.

2. The animal health, performance, fitness, training regimen, and breeding potential assessment system of claim 1, wherein the instructions stored in the memory storage unit further comprise instructions to generate consultation materials with infographics, video, diagnosis, prescriptions, imaging results, laboratory results, racing history, training history, health history, treatment options, rehabilitation markers, prognosis and follow up recommendations.

3. The animal health, performance, fitness, training regimen, and breeding potential assessment system of claim 1, wherein the instructions to provide treatment and reference information based on the diagnosis of the subject animal comprises further instructions to provide the treatment and reference information and the treatment recommendation to the trained expert system in connection with scans of other animals.

4. The animal health, performance, fitness, training regimen, and breeding potential assessment system of claim 1, wherein the plurality of posts surrounding the target area of the scanning enclosure are configured to scale up and down to accommodate a size of the subject animal.

5. The animal health, performance, fitness, training regimen, and breeding potential assessment system of claim 4, wherein the subject animal is one of a horse, a bovine, an ostrich, a human, and another animal.

6. The animal health, performance, fitness, training regimen, and breeding potential assessment system of claim 1 further comprising a pressure plate positioned at a ground level of the target area, wherein the pressure plate is configured to detect weight pressure of the subject animal when the subject animal is positioned on the pressure plate for at least a threshold time duration, wherein the pressure plate is further configured to provide differential weight pressure data to a pressure plate module of the scanner box computing device based on the detected weight pressure of different parts of the subject animal.

7. The animal health, performance, fitness, training regimen, and breeding potential assessment system of claim 6, wherein the threshold time duration is one second, wherein the instructions stored in the data storage of the scanner box computing device comprise instructions to receive the differential weight pressure data and identify gait of the subject animal based on weight pressure differences between different parts of the subject animal.

8. The animal health, performance, fitness, training regimen, and breeding potential assessment system of claim 1, wherein the plurality of scanner devices further comprise a video camera configured to capture thermographic video of the subject animal in motion at a steady pace through the target area, wherein the instructions stored in the data storage of the scanner box computing device comprise instructions to receive the thermographic video captured by the video camera, process the thermographic video, and provide photogrammetric information of the subject animal in motion through the target area at the steady pace.

9. The animal health, performance, fitness, training regimen, and breeding potential assessment system of claim 8, wherein the instructions stored in the data storage of the scanner box computing device further comprise instructions to provide, over the secure high-speed internet wireless router and by way of the wireless device of the scanner box computing device, the captured thermographic imagery and video and the photogrammetric information and the additional classified heterogeneous information about the subject animal to the particular external device in the plurality of networked devices.

10. The animal health, performance, fitness, training regimen, and breeding potential assessment system of claim 9, wherein the particular external device comprises an augmented reality goggles device that is operable by the SME and connects to the secure high-speed internet wireless router, wherein the augmented reality goggles device presents augmented views of the subject animal generated in real-time upon receiving, from the secure high-speed internet wireless router, the captured thermographic imagery and video and photogrammetric information and the additional classified heterogeneous information about the subject animal for on-site viewing by the SME.

11. The animal health, performance, fitness, training regimen, and breeding potential assessment system of claim 1, wherein the plurality of networked devices comprises a virtual reality headset.

12. The animal health, performance, fitness, training regimen, and breeding potential assessment system of claim 1, wherein the plurality of networked devices comprises a hosted AI diagnosis server.

* * * * *